(12) United States Patent
Rantala

(10) Patent No.: US 6,709,400 B1
(45) Date of Patent: Mar. 23, 2004

(54) SYSTEM AND METHOD FOR THE MEASUREMENT OF CARDIAC OUTPUT

(75) Inventor: Börje Rantala, Helsinki (FI)

(73) Assignee: Instrumentarium Corp., Helsinki (FI)

(*) Notice: Subject to any disclaimer, the term of this patent is extended or adjusted under 35 U.S.C. 154(b) by 21 days.

(21) Appl. No.: 10/089,267

(22) PCT Filed: Sep. 29, 2000

(86) PCT No.: PCT/FI00/00839
§ 371 (c)(1),
(2), (4) Date: Mar. 27, 2002

(87) PCT Pub. No.: WO01/22875
PCT Pub. Date: Apr. 5, 2001

(30) Foreign Application Priority Data

Sep. 29, 1999 (FI) .............................. 19992093

(51) Int. Cl.[7] ................................ A61B 5/02
(52) U.S. Cl. ....................... 600/526; 600/505
(58) Field of Search ................ 600/504, 508, 600/526, 300, 301, 549, 505, 585; 128/925

(56) References Cited

U.S. PATENT DOCUMENTS

| | | |
|---|---|---|
| 5,139,021 A | 8/1992 | Sekii et al. |
| 5,305,760 A | 4/1994 | McKown et al. |
| 5,509,424 A | 4/1996 | Al-Ali |
| 5,636,638 A | 6/1997 | Carlson et al. |
| 5,701,908 A | 12/1997 | Carlson et al. |
| 5,954,659 A | 9/1999 | Curley et al. |

*Primary Examiner*—Max F. Hindenburg
*Assistant Examiner*—Navin Natnithithadha
(74) *Attorney, Agent, or Firm*—Andrus, Sceales, Starke & Sawall, LLP

(57) ABSTRACT

The invention concerns a system for the measurement of cardiac (1) output. The system comprises a heating resistor (2) placed in the vena cava (6), a temperature sensor (5) placed in the pulmonary trunk (4), an isolation interface (12) for separating an isolated side (14) and a non-isolated side according to patient potential, a power source (11) which is placed on the non-isolated side and produces the energy to be supplied to the heating resistor (2), and measuring elements (18, 19, 20) for the measurement of the power supplied to the heating resistor 92). According to the invention, the power measuring (18, 19, 20) elements are disposed on the isolated side (14), allowing the effective power supplied to the heating resistor (2) to be computed as accurately as possible.

20 Claims, 2 Drawing Sheets

SYSTEM AND METHOD FOR THE MEASUREMENT OF CARDIAC OUTPUT

CROSS REFERENCE TO RELATED APPLICATION

The present application is the U.S. national stage application of International Application PCT/F100/00839, filed Sep. 29, 2000, which international application was published on Apr. 5, 2001 as International Publication No. WO 01/22875. The International Application claims priority of Finnish Patent Application No. 19992093, filed Sep. 29, 1999.

The present invention relates to medical measuring systems. In particular, the invention concerns a system and method for the measurement of cardiac output.

BACKGROUND OF THE INVENTION

For the measurement of cardiac output (CO), two methods are previously known. In the single-dose method, a dose of salt solution at a temperature differing from blood temperature is introduced into the patient's vena cava or right ventricle. The salt solution alters the temperature of the blood flowing through the heart, producing a thermal impulse in the blood circulation. The thermal impulse is measured from an artery using e.g. a thermistor connected to a Swan-Ganz catheter. Cardiac output can be computed on the basis of the time of propagation of the thermal impulse.

In the other method, a thermal impulse is generated by producing heat pulses in the blood in a vein e.g. by means of a heating resistor introduced into the vein via a catheter. For continuous cardiac output (CCO) measurement, the blood temperature is changed continuously. The cardiac output can be computed by comparing the temperature change detected by a thermistor in an artery to the change in the heating power supplied to the heating resistor.

Figure 1:
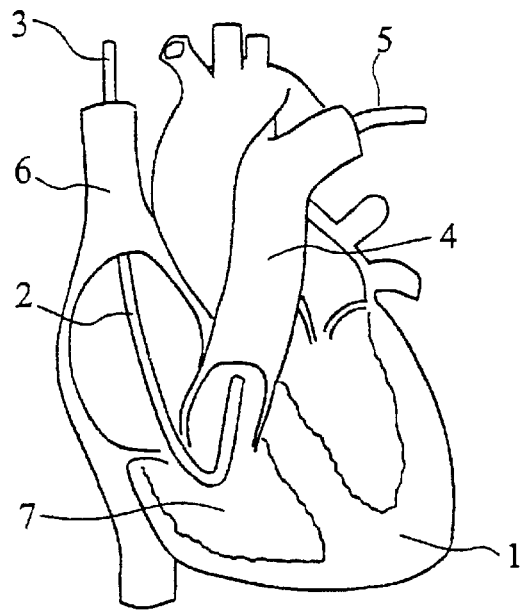

FIG. 1 presents a simplified cross-sectional view of the heart 1 and a catheter 3 as described above, which has been introduced via the vena cava 6 into the right ventricle 7 and further into the pulmonary trunk 4. The catheter comprises a heating resistor 2 placed in the vena cava 6 and a temperature sensor 5 placed in the pulmonary trunk 4.

The CCO devices currently used are bulky because they use conventional technical solutions in their power supply circuits. To achieve a 10% accuracy in measuring the cardiac output, a power impulse of an accuracy of 1% is required. To ensure the safety of the patient, the heater of the catheter is typically powered using an alternating current at about 100 kHz. Low frequencies or a direct-current component in the electric current supplied to the heart may confuse the operation of the nervous system, which is particularly hazardous. The maximum values of the power impulses are typically 10 . . . 15 W. Galvanic decoupling has to be provided between the potentials of the power supply and the patient.

As the heating resistor and the cable connected to it have some inductance, prior-art solutions use a sinusoidal wave to minimize the effect of harmonics generated as a result of variation in the phase shift introduced by the catheter or the cable.

The source used to obtain a 100-kHz sinusoidal thermal impulse is generally an isolated chopper producing a floating-power rectangular main wave. The main wave is filtered using a large passive LC low-pass filter to obtain a sinusoidal wave to be applied to the catheter of the patient. As the capacitances vary, the filtering requires accurate calibration. Since passive filtering is used and calibration can only be performed before the measurement, prior-art systems cannot provide complete certainty regarding possible parameters varying during the measurement.

Specification U.S. Pat. No. 5,636,638 discloses an electric power amplifier used in CCO measurement. In the solution presented in this specification, the power supplied to the heating resistor is measured on the non-isolated side on the basis of current and voltage values. Correspondingly, the conversion from a rectangular wave into a sinusoidal wave is also performed on the non-isolated side. On the isolated side, the state and calibration of the catheter are monitored using a specific comparator circuit, from which the data is passed into a microprocessor controlling the system. The comparator circuit comprises a calibration resistor, and the value obtained from this resistor is used as a calibration reference.

The object of the present invention is to eliminate the drawbacks referred to above or at least to significantly alleviate them. A specific object of the invention is to disclose a new type of distributed system and method for the measurement of cardiac output that will allow a better control of the power supplied to the heating resistor. In addition, the present invention improves the technical diagnosis of the system. Intelligent functions implemented on the isolated side improve the reliability of the system as the last monitoring point is as close to the patient as possible. Thus, patient safety is also improved.

BRIEF DESCRIPTION OF THE INVENTION

The basic idea of the invention is a distributed system for the measurement of cardiac output in which intelligent components are disposed on the patient side of an isolation interface.

The invention concerns a system for the measurement of cardiac output which comprises a temperature sensor placed in the vena cava and a heating resistor placed in the pulmonary trunk. The essential point about the placement of the temperature sensor is that its position in the blood vascular system is after the heating resistor or salt solution with respect to the direction of flow of blood. Moreover, the system comprises an isolation interface serving to separate an isolated side and a non-isolated side according to the potential of the patient. The energy to be supplied into the heating resistor is produced using a power source placed on the non-isolated side. According to the invention, the elements for the measurement of the power supplied to the heating resistor are disposed on the isolated side. The measuring elements are preferably current and voltage measuring elements, by means of which the effective power and the reactive power supplied to the catheter can be separated from each other.

Depending on the application, the effective power can be computed on different sides of the isolation interface. In an embodiment, the means for computing the effective power supplied to the heating resistor are disposed on the non-isolated side; in another embodiment, on the isolated side.

In an embodiment of the invention, the power measuring elements comprise a voltage measuring element and a current measuring element which measure the instantaneous value of the relevant quantity. In an embodiment, the power measuring elements comprise an A/D converter whose sampling frequency exceeds twice the highest substantial harmonic frequency of the rectangular wave produced by the power source. In an embodiment, the power measuring elements comprise an A/D converter whose sampling frequency is based on sub-Nyquist sampling. An embodiment of the invention comprises a low-pass filter disposed on the isolated side for filtering the rectangular wave fed to the heating resistor. The filtered power signal need not be a perfectly sinusoidal wave. The essential point is that the fast transients of the rectangular wave are sufficiently retarded to allow the application of lower requirements regarding the operating rate of the A/D converter used in the system. The frequency spectrum of an ideal rectangular wave is infinite, so it is not directly applicable as such for an advantageous A/D converter having suitable properties in other respects.

In an embodiment, the system comprises means for producing a technical diagnosis of the system from the reactive power. From changes in the reactive power, it is possible to detect e.g. a damaged cable insulation. This allows the system diagnostics to take appropriate steps e.g. by interrupting the supply of power to the catheter.

In an embodiment, the isolated side comprises means for the measurement of the resistance of the heating resistor. The resistance of the heating resistor changes as a function of temperature, so it needs to be known to allow the actual heating power to be computed. In an embodiment, the isolated side is provided with means for converting the blood temperature data into a digital form. These means comprise e.g. a suitable A/D converter, and in another embodiment they additionally comprise means for converting said digital form e.g. into a form acceptable to a suitable bus protocol.

In a preferred embodiment, the system comprises a microcontroller disposed on the isolated side. In this case, the means described above belong to an embedded system in which some of the functions are implemented via software. In this context, 'microcontroller' refers to a processor-controlled device capable of controlling an external system. The microcontroller may also consist of e.g. a suitable micro-processor, a programmable logic circuit or an application specific integrated circuit (ASIC).

Moreover, the invention concerns a system which comprises means for changing the temperature of the blood in the vena cava, a temperature sensor placed in an artery and an isolation interface serving to separate an isolated side and a non-isolated side according to patient potential. According to the invention, the isolated side is provided with means for converting the blood temperature data into a digital form. The system on the isolated side is independent of the system used to produce a change in blood temperature. It may be e.g. a separate module collecting blood temperature data. Using a separate management system, it is possible to combine information obtained from several different modules, allowing the cardiac output to be computed from the temperature data.

The invention further concerns a method for the measurement of cardiac output in a system as described above. In the method, the power supplied to the heating resistor is measured on the isolated side. In an embodiment, the effective power supplied to the heating resistor is computed on the non-isolated side; in another embodiment, on the isolated side. For the computation of the power, preferably the instantaneous value of the voltage and current is measured.

In an embodiment, the sampling frequency used for the power measurement exceeds twice the highest substantial harmonic frequency of the rectangular wave produced by the power source. In another embodiment, the sampling frequency used for the power measurement is based on sub-Nyquist sampling. The rectangular wave to be fed to the heating resistor is low-pass-filtered preferably on the isolated side. In an embodiment, a technical diagnosis of the system is produced using the reactive power value obtained in the power measurement. In an embodiment, the resistance of the heating resistor is measured on the isolated side. The resistance can be derived according to Ohm's law from the voltage and current wave forms obtained in the power measurement.

The blood temperature data is preferably converted into a digital form on the isolated side. In an embodiment, a microcontroller is provided on the isolated side.

As compared with prior art, the advantages of the present invention include the fact that, by placing the active components on the isolated side, a cheaper implementation can be achieved. The power signal transmitted across the isolation interface need not be exactly sinusoidal to minimize the effects of unwanted harmonic components. The filtering can be performed using cheaper components. The present invention also makes it possible to transfer the measurement result in a digital form across the isolation interface. The advantage thus achieved is considerable; the signal level does not deteriorate in crossing the interface, and the technical operation required for the crossover is quite simple. In addition, the system improves patient safety in the form of an improved system diagnosis. As the current and voltage waveforms are monitored at a point just before the catheter, the control data needed for the regulation of the system as a whole is as accurate as possible.

In a solution according to the present invention, no separate calibration resistors are needed on the isolated side because the system receives the information directly from the isolated side. A distributed system is also flexible; different functions can be combined to form distinct functional units, modules that can be removed or added to the system as necessary.

List of Illustrations

Figure 2:
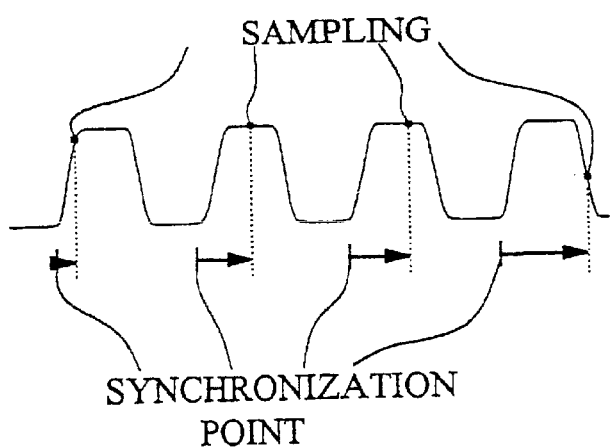

In the following, the invention will be described by the aid of a few examples of its embodiments with reference to the attached drawing, wherein FIG. 1 presents a simplified cross-sectional view of the heart and a catheter as used in the invention;

FIG. 2 presents an example of sub-Nyquist sampling; and

Figure 3:
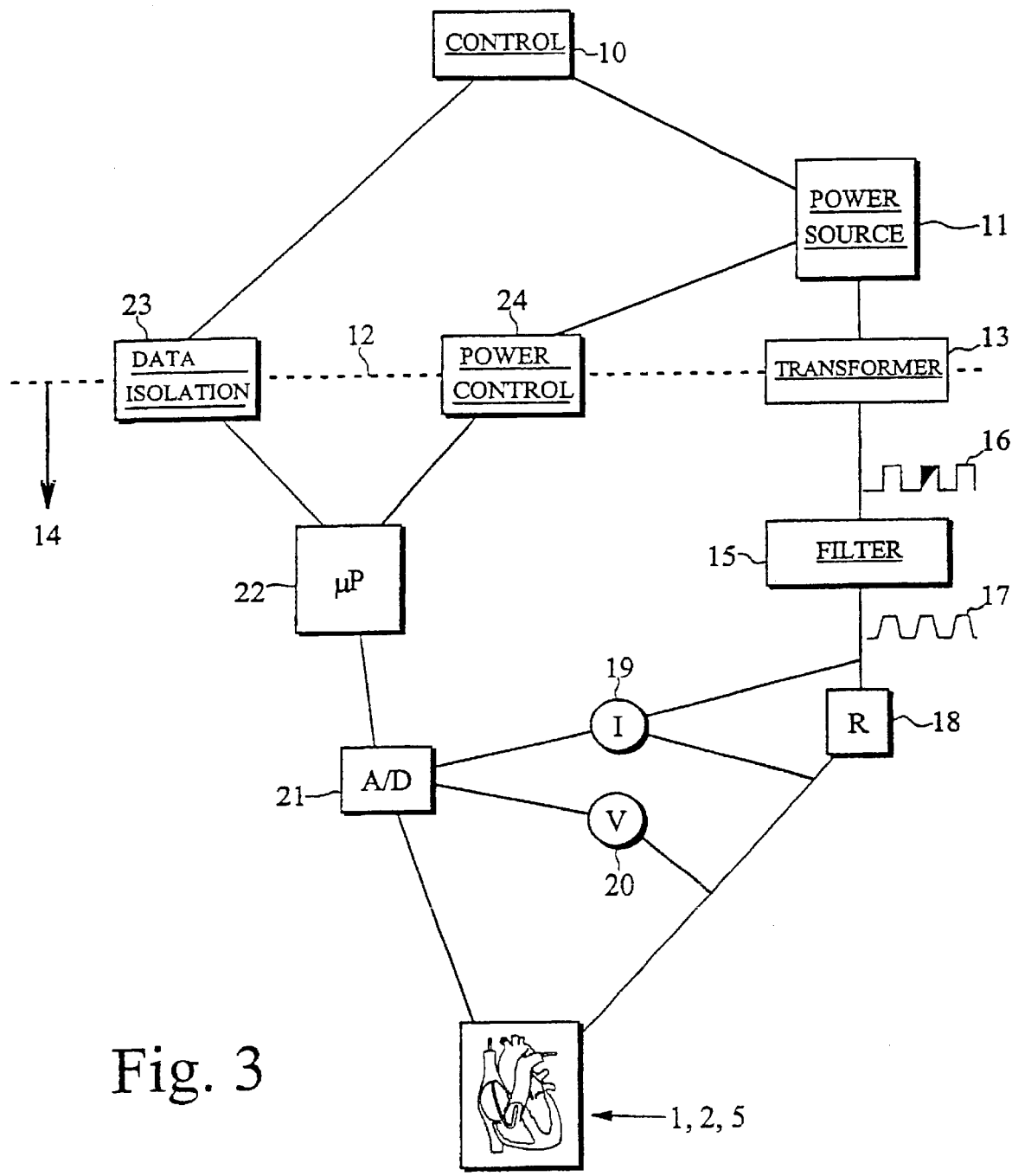

FIG. 3 presents a simplified functional block diagram of a system according to the present invention.

DETAILED DESCRIPTION OF THE INVENTION

FIG. 3 presents a functional block diagram representing a system according to the invention. In this example, the host of the system is a control module 10 which controls the entire measuring operation while simultaneously supervising several functional units connected to the system. In the measurement, temperature changes, i.e. thermal impulses are produced in the blood flowing through the right ventricle of the heart. By analyzing the changes, a cardiac output value is obtained. In the example, the duration of the thermal impulse is one second. In this case, the control module 10 turns on the output of the power source 11 for one second. The output of the power source 11 is a rectangular-wave a.c. signal having a frequency of about 100 kHz and a power level of 10 . . . 15 W.

In medical measuring systems, an essential requirement is that power and measuring equipment connected to the mains potential be isolated from the electric potential of the patient. The output of the power source 11 is isolated from the patient by an isolation interface 12, which in this example is implemented as an isolating transformer 13. The power source 11 and the isolation interface can also be implemented as an integrated system in ways known to the skilled person. The aim is to transfer the power signal across the isolation interface 12 as a waveform as smooth as possible.

On the isolated side 14, the rectangular-wave power signal is filtered by a low-pass filter 15. The purpose of the filtering is to retard the fast transients of the rectangular wave and eliminate unwanted oscillations, thus making it easier to monitor the power signal in the next stage. The figure shows the power signal waveform before 16 and after 17 the filtering. The low-pass filter 15 can be implemented in a simple manner using resistances and capacitances without any inductive elements, which would be difficult to fit in.

The power signal is passed through a shunt resistor 18, so the current supplied to the heating resistor 2 is obtained according to Ohm's law using a current sensor 19 connected across the shunt resistor 18. The voltage applied to the heating resistor 2 can be measured in a corresponding manner using a voltage sensor 20. The instantaneous values of the voltage and current are passed to an A/D converter 21, which converts the values into a digital form. The A/D converter must have a sampling frequency that allows the waveform of the current and voltage supplied to the heating resistor 2 to be reconstructed with a maximum fidelity. The sampling frequency may be selected according to the Nyquist criterion, which means that the sampling frequency has to be at least twice the highest substantial harmonic frequency.

FIG. 2 presents an example of sub-Nyquist sampling, which is used in an embodiment of the invention. The frequency needed in the sampling is reduced by a method in which a predetermined synchronization point is known. The sampling is timed by adding some time after each synchronization point before taking a sample. The method described above is particularly practical because in the present invention the signal to be measured is a substantially regular signal. By reducing the sampling frequency, the power consumption of the measuring system is reduced. At the same time, the component costs of the entire system are reduced as the generation of the operating voltage is simplified and the requirements regarding the properties of the A/D converter are reduced.

The output of the A/D converter 21 is taken to a microcontroller 22, which is disposed on the isolated side 14. The microcontroller 22 as well as the A/D converter 21 are connected to a floating potential. The microcontroller 22 computes the effective power supplied to the heating resistor 2 by multiplying the waveforms of the current and voltage by each other. As the A/D converter 21 receives the current and voltage values as simultaneous instantaneous values, the actual effective power can be calculated by multiplying the values by each other. Thus, the system is independent of any phase difference between current and voltage, which may arise in the transmission cable e.g. as a result of parasitic inductances and capacitances. With this arrangement, complicated calibration is avoided as the system has continuously updated information regarding the power supplied to the heating resistor 2.

The value of the effective power being known, the reactive power transmitted in the system can be correspondingly calculated from the known initial values. The reactive power component is not transmitted to the heating resistor 2; instead, it wastes energy mainly by heating the transmission lines. By experimenting, predetermined limits within which the value of the reactive power component should remain can be determined for the measuring system. If the reactive power component changes suddenly or is outside the limit values, the system diagnostics will detect the error situation and take appropriate measures. By examining the states of change of the reactive power component, it is possible to program the microcontroller 22 by defining predetermined limit values or situations in which it is to inform the control module 10 about a disorder or the cause of a fault. For example, anomalies such as damaged transmission cable insulation, disturbance of the measuring operation due to external electromagnetic radiation or the like may result in a reactive power component deviating from its normal value. Depending on the degree of seriousness of the situation, the microcontroller 22 can e.g. shut off the supply of electricity to the power source 11 or add to the measurement result an indication of unreliable measurement.

The measuring system also comprises a temperature sensor for monitoring blood temperature in the blood circulation after the thermal impulse. The temperature data produced by the temperature sensor is transmitted to the A/D converter 21, which passes the digital temperature data further to the microcontroller 22. Depending on the system, the cardiac output value may also be calculated by the microcontroller 22. In another system, the microcontroller 22 processes the data to give it a form consistent with a suitable bus protocol, and the arithmetic operations are performed by a computing unit in the distributed system. The digital data is transmitted across the isolation interface via a data adapter 23, which in one embodiment is based on the action of an opto-isolator. Other methods known in the art are also applicable for implementing the isolation.

The microcontroller 22 on the isolated side 14 can also be operated directly under control of the power source 11. In this case, the control data must be transmitted to the power source 11 via a power control component 24. The power control component 24 also implements the isolation required in the system. This solution makes it possible to implement the measuring arrangement as a more compact functional whole in which a single module takes care of the measurement of cardiac output.

The above-described system can also be used in conjunction with the single-dose method. In this case, the measuring arrangement comprises no heating resistor 2; instead, the control module 10 or the person performing the measurement controls the activity of a dose of salt solution. The salt solution produces a change in blood temperature, and the change is detected by the temperature sensor. The information obtained from the temperature sensor is correspondingly transmitted to the microcontroller 22, allowing the cardiac output value to be computed in the manner described above.

The structures described above can also be combined to form different functional units. In one embodiment, the same module comprises functions for both monitoring the power supplied to the heating resistor 2 and monitoring the temperature sensor. In another embodiment, one module only comprises means for monitoring the temperature sensor. Such a module is applicable for use both in conjunction with the use of salt solution and in conjunction with the use of a heating resistor 2.

The invention is not restricted to the examples of its embodiments described above; instead, many variations are possible within the scope of the inventive idea defined in the claims.

What is claimed is:

1. A system for the measurement of cardiac output, said system comprising:
   a heating resistor, which is placed in the vena cava;
   a temperature sensor, which is placed in the pulmonary trunk;
   an isolation interface for separating an isolated side and a non-isolated side according to patient potential;
   a high frequency alternating current power source, which is placed on the non-isolated side and which produces a high frequency alternating current energy to be supplied to the heating resistor; and
   measuring elements for the direct measurement of the high frequency alternating current power supplied to the heating resistor wherein the power measuring elements are disposed on the isolated side.

2. A system as defined in claim 1, wherein the system comprises means placed on the isolated side for computing the effective power supplied to the heating resistor.

3. A system as defined in claim 1, wherein the power measuring elements comprise a voltage measuring element and a current measuring element, said elements, measuring the instantaneous value of the relevant quantity.

4. A system as defined in claim 1, wherein the power measuring elements comprise an A/D converter whose sampling frequency exceeds twice the highest substantial harmonic frequency of a rectangular wave produced by the high frequency alternating current power source.

5. A system as defined in claim 1, wherein the power measuring the elements comprise an A/D converter whose sampling frequency is based on sub-Nyquist sampling.

6. A system as defined in claim 1, wherein the system comprises a low-pass filter disposed on the isolated side for filtering a rectangular wave supplied to the heating resistor.

7. A system as defined in claim 1, wherein the system comprises means for producing a technical diagnosis of the system from the reactive power.

8. A system as defined in claim 1, wherein the system comprises means placed on the isolated side for measuring the resistance of the heating resistor.

9. A system as defined in claim 1, wherein the system comprises means placed on the isolated side for converting blood temperature data into a digital form.

10. A system as defined in claim 1, wherein the system comprises a microcontroller placed on the isolated side.

11. A method for the measurement of cardiac output in a system, the method comprising the steps of:
   placing a heating resistor in the vena cava;
   placing a temperature sensor in the pulmonary trunk;
   providing an isolation interface for separating an isolated side and a non-isolated side according to patient potential;
   placing a high frequency alternating current power source on the non-isolated side which produces a high frequency alternating current energy to be supplied to the heating resistor; and
   providing measuring elements for the direct measurement of the high frequency alternating current power supplied to the heating resistor, wherein the high frequency alternating current power supplied to the heating resistor is measured on the isolated side.

12. A method as defined in claim 11, wherein the effective power supplied to the heating resistor is computed on the isolated side.

13. A method as defined in claim 11, wherein, to compute the power, the instantaneous values of the voltage and of the current are measured.

14. A method as defined in claim 11, wherein the sampling frequency used in measuring the power exceeds twice the highest substantial harmonic frequency of a rectangular wave produced by the high frequency alternating current power source.

15. A method as defined in claim 11, wherein the sampling frequency used in the measurement of power is based on sub-Nyquist sampling.

16. A method as defined in claim 11, wherein the rectangular wave to be supplied to the heating resistor is low-pass-filtered on the isolated side.

17. A method as defined in claim 11, wherein a technical diagnosis of the system is produced on the basis of the reactive power.

18. A method as defined in claim 11, wherein the resistance of the heating resistor is measured on the isolated side.

19. A method as defined in claim 11, wherein blood temperature data is converted into a digital form on the isolated side.

20. A method as defined in claim 11, wherein a microcontroller is provided on the isolated side.

* * * * *